United States Patent
Pugh

(10) Patent No.: US 6,945,943 B2
(45) Date of Patent: Sep. 20, 2005

(54) ANALYTE CONCENTRATION DETERMINATION DEVICES AND METHODS OF USING THE SAME

(75) Inventor: Jerry T. Pugh, Mountain View, CA (US)

(73) Assignee: LifeScan, Inc., Milpitas, CA (US)

( * ) Notice: Subject to any disclaimer, the term of this patent is extended or adjusted under 35 U.S.C. 154(b) by 313 days.

(21) Appl. No.: 10/137,598

(22) Filed: May 1, 2002

(65) Prior Publication Data

US 2003/0208140 A1 Nov. 6, 2003

(51) Int. Cl.[7] .............................. A61B 5/00; B65D 81/00
(52) U.S. Cl. ....................................................... 600/584
(58) Field of Search ................................ 600/584, 583, 600/573, 549, 504, 345, 322; 422/56, 50, 55, 82.05; 435/14

(56) References Cited

U.S. PATENT DOCUMENTS

| | | |
|---|---|---|
| 720,906 A | 2/1903 | Eilrich et al. |
| 4,553,541 A | 11/1985 | Burns |
| 4,637,403 A | 1/1987 | Garcia et al. |
| 4,648,408 A | 3/1987 | Hutcheson et al. |
| 4,787,398 A | 11/1988 | Garcia et al. |
| 5,212,879 A | 5/1993 | Biro et al. |
| 5,231,993 A | 8/1993 | Haber et al. |
| 5,314,441 A | 5/1994 | Cusack et al. |
| 5,395,387 A | 3/1995 | Burns |
| 5,439,473 A | 8/1995 | Jorgensen |
| 5,476,474 A | 12/1995 | Davis et al. |
| 5,529,581 A | 6/1996 | Cusack |
| 5,575,403 A | 11/1996 | Charlton et al. |
| 5,757,666 A | 5/1998 | Schreiber et al. |
| 5,820,570 A | 10/1998 | Erickson et al. |
| 5,879,367 A | 3/1999 | Latterell et al. |
| 5,951,492 A | 9/1999 | Douglas et al. |
| 5,951,493 A | 9/1999 | Douglas et al. |
| 5,971,941 A | 10/1999 | Simons et al. |
| 6,027,459 A | 2/2000 | Shain et al. |
| 6,071,250 A | 6/2000 | Douglas et al. |
| 6,099,484 A | 8/2000 | Douglas et al. |
| 6,228,100 B1 | 5/2001 | Schraga |
| 2003/0069509 A1 * | 4/2003 | Matzinger et al. ........... 600/504 |
| 2003/0191415 A1 * | 10/2003 | Moerman et al. ........... 600/584 |

FOREIGN PATENT DOCUMENTS

| | | |
|---|---|---|
| EP | 1 112 717 A | 7/2001 |
| WO | WO 99/44508 | 9/1999 |
| WO | WO 02/08753 A2 | 1/2002 |

* cited by examiner

Primary Examiner—Max F. Hindenburg
Assistant Examiner—Brian Szmal
(74) Attorney, Agent, or Firm—Carol M. LaSalle; Bozicevic, Field & Francis LLP

(57) ABSTRACT

Devices and methods for analyte concentration determination are provided. The subject devices have a housing having an aperture, a lancing element having a lancet held therein disposed within the housing, a manner for activating the lancing element to displace the lancet to provide an incision in an area of skin to provide physiological sample, and a manner for determining whether a sufficient amount of the physiological sample is present at the surface of the skin. The subject methods include lancing an area of skin to provide physiological sample at the surface of the area of skin, illuminating the physiological sample present at the surface of skin, detecting light reflected from the physiological sample, and determining whether the physiological sample is present in an amount sufficient for analyte concentration determination based upon the detected light. The subject invention also includes kits for use in practicing the subject methods.

4 Claims, 4 Drawing Sheets

ANALYTE CONCENTRATION DETERMINATION DEVICES AND METHODS OF USING THE SAME

FIELD OF THE INVENTION

The field of this invention is analyte concentration determination devices.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, drugs for monitoring levels of therapeutic agents, identifying illegal levels of drugs, and the like. In response to this growing importance of analyte concentration determination, a variety of analyte concentration determination protocols and devices for both clinical and home testing have been developed.

In determining the concentration of an analyte in a physiological sample, a physiological sample must first be obtained for testing. However, obtaining and testing the sample often involves cumbersome and complicated procedures. Unfortunately, successful manipulation and handling of multiple test elements, such as an analyte tester, e.g., a test strip, lancing members, meters and the like is to a great extent dependent on the visual acuity and manual dexterity of the user, which, in the case of people with diabetes for example, is subject to deterioration over the course of the disease state. In extreme cases, for people who have significant loss of sight, hand-eye coordination and fingertip sensation, testing procedures can become significantly difficult and require additional assistance from ancillary devices or personnel.

A typical procedure for making an analyte concentration measurement with the use of an analyte tester such as a tester configured as a test strip or the like involves the following actions or steps (but not necessarily in the order given): (1) removing testing supplies from a carrying case, (2) grasping the lancing device and removing a lancing device loading cap or door, (3) removing and disposing of a used lancet from the lancing device, (4) inserting a new lancet in the lancing device, (5) twisting off a protective cap from the lancet, (6) replacing the lancing device cap, (7) cocking the lancing device, (8) opening a tester vial/container, (9) removing a tester from the container and inserting or interfacing it with a meter, (10) holding the lancing device to the skin, (11) firing the lancing device, (12) removing the lancing device from the skin, (13) extracting a sample from the incised area of skin, (14) applying sample to the tester and obtaining results of the measurement; (15) disposing of the tester, (16) cleaning the test site, and (17) returning supplies to the carrying case. Of course, certain analyte measurement systems and protocols may involve fewer or more steps.

One manner of reducing the number of actions is by the use of integrated devices which combine multiple functions in order to minimize the handling of testers and/or lancing components which may lead to contamination of the components and/or injury to the user, especially in those instances where the user has diminished fingertip sensation and visual acuity. In this regard, certain tester dispensers are configured to both store and advance successive testers upon actuation. Examples of such devices for dispensing test strips are presented in U.S. Pat. Nos. 5,510,266; 5,660,791; 5,575,403; 5,736,103; 5,757,666; 5,797,693; 5,856,195 and PCT Publication WO 99/44508. Some of these test strip dispenser devices also include meter functionality for testing physiological fluid.

Another class of devices designed to decrease the number of steps required in analyte concentration determination assays includes automatic or semi-automatic lancing devices. U.S. Pat. No. 6,228,100 discloses a structure configured for sequential firing of a number of lancets, one at a time, in order to eliminate the requirement that a user remove and replace each lancet individually before and after use. However, this device does not include any tester components or functions.

Attempts have been made to combine a lancing-type device with various other components involved in the analyte concentration determination procedure in order to simplify the analyte concentration determination assay process. For example, U.S. Pat. No. 6,099,484 discloses a sampling device which includes a single needle associated with a spring mechanism, a capillary tube associated with a pusher, and a test strip. An analyzer may also be mounted in the device for analyzing the sample. Accordingly, the single needle is displaced toward the skin surface by un-cocking a spring and then retracting it by another spring. A pusher is then displaced to push the capillary tube in communication with a sample and the pusher is then released and the fluid is transferred to a test strip through the capillary tube.

U.S. Pat. No. 5,820,570 discloses an apparatus which includes a base having a hollow needle and a cover having a membrane, whereby the base and cover are connected together at a hinge point. When in a closed position, the needle is in communication with the membrane and fluid can be drawn up through the needle and placed on the membrane of the cover.

There are certain drawbacks associated with each of the above devices and techniques. For example, the devices disclosed in the aforementioned patents are configured to test the sample at a site distant from the lanced site, thereby requiring the sample to be moved from the lanced site to another area for testing. Accordingly, in the case of the '484 patent, sample is moved through a capillary tube to a test strip and in the case of the '570 patent sample is moved through the needle to a membrane. While effective at moving the sample to the site of testing, a significant amount of sample may be lost during the transport process using such methods and devices, e.g., sample may adhere to the sides of the capillary tube, needle or the like. To compensate for such sample loss, such devices require a greater amount of sample from the incision area in order to perform an accurate test at the testing area, such that oftentimes the user needs to "milk" the initial lanced site to extract the required amount of sample therefrom or may need to lance yet another site. Both options are difficult for a user suffering from diabetes and have significant pain associated with them as well.

However, in many instances, the user is not aware that an insufficient amount of sample has been contacted with the tester or additional sample can not be provided in a timely manner. In such cases, a tester is wasted as the tester having insufficient amount of sample must be discarded and another test must be performed with a new tester, thereby increasing the cost of analyte concentration determination.

As such, there is continued interest in the development of new devices and methods for use in the determination of analyte concentrations in a physiological sample. Of particular interest would be the development of integrated devices, and methods of use thereof, that are efficient, simple to use, able to determine whether a sufficient amount of sample is present before contacting the sample with a tester and which require minimal sample amounts in order to perform an accurate analyte concentration determination.

SUMMARY OF THE INVENTION

Devices and methods for determining the concentration of an analyte in a physiological sample are provided. The subject devices are meters characterized by having a housing having an aperture, a lancing element having a lancet held therein disposed within the housing, means for activating the lancing element to displace the lancet through the aperture of the housing to provide an incision in an area of skin to provide physiological sample at the surface of the incised area of skin, and means for determining whether a sufficient amount of the physiological sample is present at the surface of the incised area of skin for analyte concentration determination.

The subject methods include (1) lancing an area of skin to provide an incision in the area of skin, whereby physiological sample is provided at the surface of the area of skin, (2) illuminating the physiological sample present at the surface of skin, (3) detecting light reflected from the physiological sample, and (4) determining whether the physiological sample is present at the surface of the skin in an amount sufficient for analyte concentration determination based upon the detected reflected light. Once a sufficient amount of sample is determined to be present, a tester is contacted with the sample and the concentration of an analyte in the sample is determined. The subject invention also includes kits for use in practicing the subject methods.

DETAILED DESCRIPTION OF THE INVENTION

Figure 1:
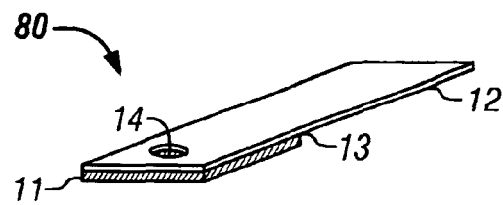
FIG. 1 shows an exemplary embodiment of a representative tester suitable for use in the subject invention configured as a test strip.

Devices and methods for determining the concentration of an analyte in a physiological sample are provided. The subject devices are meters characterized by having a housing having an aperture, a lancing element having a lancet held therein disposed within the housing, means for activating the lancing element to displace the lancet through the aperture of the housing to provide an incision in an area of skin to provide physiological sample at the surface of the incised area of skin, and means for determining whether a sufficient amount of the physiological sample is present at the surface of the incised area of skin for analyte concentration determination.

The subject methods include (1) lancing an area of skin to provide an incision in the area of skin, whereby physiological sample is provided at the surface of the area of skin, (2) illuminating the physiological sample present at the surface of skin, (3) detecting light reflected from the physiological sample, and (4) determining whether the physiological sample is present at the surface of the skin in an amount sufficient for analyte concentration determination based upon the detected reflected light. Once a sufficient amount of sample is determined to be present, a tester is contacted with the ample and the concentration of an analyte in the sample is determined. The subject invention also includes kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a tester" includes a plurality of such testers and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject devices are described first. Next, a description of the subject methods is provided, followed by a review of kits which include the subject devices.

Devices

As summarized above, devices are provided for determining the concentration of an analyte in a physiological sample. Particularly, analyte tester meter devices are provided that are capable of creating an incision in an area of skin and determining whether a sufficient amount of sample is present at the surface of the skin at the incised area to provide an accurate analyte concentration determination. Using such a device advantageously enables a user to perform an analyte concentration determination test only in those instances where a sufficient amount of sample is present, thereby avoiding contacting a tester with an insufficient amount of sample. Accordingly, using the subject devices prevents the need to discard or waste a tester due to an insufficient amount of sample applied thereto, thereby reducing the cost of analyte concentration determination.

The subject invention is suitable for determining analyte concentration using a wide variety of testers. As the subject devices are optical or photometric-type devices, the testers used with the subject meters may be correctly characterized as optical, colorimetric or photometric (used herein interchangeably) type testers as are known in the art. Such testers find use in the determination of a wide variety of different analyte concentrations, where representative analytes include, but are not limited to, glucose, cholesterol, lactate, alcohol, and the like. In many embodiments, the testers used with the subject invention are used to determine the glucose concentration in a physiological sample, e.g., interstitial fluid, blood, blood fractions, constituents thereof, and the like.

In further describing the subject invention, a review of representative calorimetric testers is provided first to provide a proper foundation for the subject invention, where such a review is by way of example and is not intended to limit the scope of the invention. In other words, it will be apparent that a wide variety of testers, including, but not limited to, the representative calorimetric testers described herein, may be suitable for use with the present invention. The review of suitable testers is followed by a description of the subject tester meter devices and the subject methods. Finally, a description of kits for use in practicing the subject methods is provided.

Representative Testers

Referring now to the figures, where like numerals represent like components or features, FIG. 1 shows an exemplary embodiment of a representative calorimetric reagent tester 80 employed in these embodiments of the subject invention. Tester 80 is generally made up of at least the following components: a matrix 11 for receiving a sample, a reagent composition (not shown as a structural component) that typically includes one or more members of an analyte oxidation signal producing system and a support element 12. FIG. 1 shows tester 80 having matrix 11 positioned at one end of support element 12 with an adhesive 13 such that it is configured as a test strip. A hole 14 is present in the support element 12 in the area of matrix 11 in which a sample can be applied to one side of the matrix 11 and a reaction can be detected on an opposite side of matrix 11. The components of an exemplary, representative tester will now be described in more detail.

Matrix

Matrix 11 that is employed in the testers is an inert matrix which provides a support for the various members of the signal producing system, described below, as well as the light absorbing or chromogenic product produced by the signal producing system, i.e., the indicator. Matrix 11 is configured to provide a location for the physiological sample, e.g., blood, application and a location for the detection of the light-absorbing product produced by the indicator of the signal producing system. As such, matrix 11 is one that is permissive of aqueous fluid flow through it and provides sufficient void space for the chemical reactions of the signal producing system to take place. A number of different matrices have been developed for use in various analyte detection assays, which matrices may differ in terms of materials, dimensions and the like, where representative matrices include, but are not limited to, those described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

In principle, the nature of matrix 11 is not critical to the tester and therefore is chosen with respect to other factors, including the nature of the instrument which is used to read the tester, convenience and the like. As such, the dimensions and porosity of the matrix may vary greatly, where matrix 11 may or may not have pores and/or a porosity gradient, e.g. with larger pores near or at the sample application region and smaller pores at the detection region. Materials from which matrix 11 may be fabricated vary, and include polymers, e.g. polysulfone, polyamides, cellulose or absorbent paper, and the like, where the material may or may not be functionalized to provide for covalent or non-covalent attachment of the various members of the signal producing system.

Signal Producing System

In addition to matrix 11, the testers further include one or more members of a signal producing system which produces a detectable product in response to the presence of analyte, which detectable product can be used to derive the amount of analyte present in the assayed sample. In the testers, the one or more members of the signal producing system are associated, e.g., covalently or non-covalently attached to, at least a portion of (i.e., the detection region) the matrix, and in many embodiments to substantially all of the matrix.

In certain embodiments, e.g., where glucose is the analyte of interest, the signal producing system is an analyte oxidation signal producing system. By analyte oxidation signal producing system is meant that in generating the detectable signal from which the analyte concentration in the sample is derived, the analyte is oxidized by one or more suitable enzymes to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the testers are also correctly characterized as hydrogen peroxide based signal producing systems.

As indicated above, the hydrogen peroxide based signal producing systems include an enzyme that oxidizes the analyte and produces a corresponding amount of hydrogen peroxide, whereby corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those embodiments where the reagent tester is designed for the detection of glucose concentration, the first enzyme is glucose oxidase. The glucose oxidase may be obtained from any convenient source, e.g. a naturally occurring source such as *Aspergillus niger* or Penicillum, or recombinantly produced.

A second enzyme of the signal producing system may be an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds, e.g., substrates, are ones that are either formed or decomposed by the hydrogen peroxide in the presence of the peroxidase to produce an indicator dye that absorbs light in a predetermined wavelength range. Typically, the indicator dye absorbs strongly at a wavelength different from that at which the sample or the testing reagent absorbs strongly. The oxidized form of the indicator may be a colored, faintly-colored, or colorless final product that evidences a change in color of the matrix. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

Support Element

Matrix 11 is usually attached to a support element 12. Support element 12 may be of a material that is sufficiently rigid to be inserted into an automated device such as a meter without undue bending or kinking. Matrix 11 may be attached to support element 12 by any convenient mechanisms, e.g., clamps, adhesive, etc., herein shown attached using an adhesive 13. In many embodiments, support member 12 is made of material such as polyolefins, e.g., polyethylene or polypropylene, polystyrene or polyesters. The length of the support element 12 typically dictates or corresponds to the length of the tester.

As described above, support element 12 is usually configured to enable a tester to be used with or inserted into a meter. As such, support element 12, and thus tester may assume a variety of shapes and sizes, where the exact size and shape are dictated in part by the device with which the tester is used.

In using such a tester, sample is allowed to react with the members of the signal producing system to produce a detectable product that is present in an amount proportional to the initial amount present in the sample. The amount of sample that is introduced to matrix 11 of the test strip may vary, but generally ranges from 5.0 to about 10.0 $\mu l$. The sample may be introduced to matrix 11 using any convenient protocol, where the sample may be injected, allowed to wick, or be otherwise introduced. The amount of detectable product, i.e., signal produced by the signal producing system, is then determined and related to the amount of analyte in the initial sample. See U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference for a description of the above-described reaction, detection and relating steps.

Examples of such colorimetric reagent testers suitable for use with the subject invention include, but are not limited to, those described in U.S. Pat. Nos. 5,049,487; 5,563,042; 5,753,452; 5,789,255, the disclosures of which are herein incorporated by reference.

Analyte Concentration Determination Devices

As described above, the subject invention includes analyte concentration determination devices, i.e., optical meter devices, that automatically determine the concentration of an analyte in a physiological sample applied to a tester, such as the type of tester described above or the like. A feature of the subject devices is that they are capable of determining whether a sufficient amount of sample is present at the incision site, i.e., at the surface if the skin where an incision has been made, to perform an accurate analyte concentration determination. In other words, the subject meters determine the sufficiency of sample size before any sample is contacted with a tester, thereby conserving testers for use only in instances where a sufficient amount of sample is present. In many embodiments of the subject devices, the device is capable of bringing a tester into contact with the sufficient amount of sample at the site of the incision, thereby eliminating the need to move or transfer the sample to the site of the tester, which oftentimes results in significant loss of sample to the transfer element.

Figure 2:
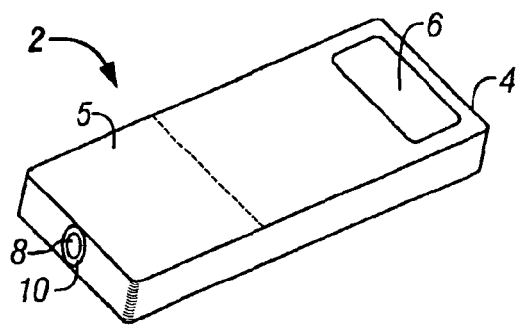
FIG. 2 shows an exterior view of an exemplary embodiment of a subject device.

FIG. 2 shows a perspective view of the exterior of a subject device. Accordingly, device 2 includes housing 4 having reporting element 6 positioned on the exterior thereof for communicating information to the user such as results of sample amount determination and analyte concentration. Accordingly, reporting element 6 may take various hard copy and soft copy forms. Usually it is a visual display such as a liquid crystal display (LCD) or light emitting diode (LED) display, but it may also be a tape printer, audible signal, or the like. Housing 4 also has aperture 8 positioned through a wall or side thereof to provide an opening from the interior to the exterior of the housing, for example to enable a lancet to protrude therethrough to make an incision in an area of skin and for sample collection and also for light to pass through. Housing 8 may also include a physiological sample promoting element 10 that is typically positioned adjacent aperture 8, and usually is configured as a ring or the like positioned around at least a part of the perimeter of aperture 8, as will be described in greater detail below. Housing 4 also has panel or cover 5 through which the interior of housing 4 may be accessed by the user, for example to load and/or remove testers and/or a disposable lancet therein. It will be apparent that other access means may be employed as well. Panel 5 is constructed to be moveable from a closed to an opened position by any convenient means. For example, panel 5 may be slideably moved, hingedly affixed to housing 4, etc.

The shape of housing 4 will necessarily vary depending on a variety of factors, where such factors include, but are not limited to, the type and size of the tester used therewith and the number of such testers that are stored in the meter, for example in a cartridge or casing or the like. Usually, housing 4 is shaped to be easily and comfortably, e.g., ergonomically, held in a user's hand. FIG. 2 shows housing 4 having a rectangular shape, but other shapes are possible as well. For example, housing 4 may be of a square, cylindrical, circular, disc, or elliptical shape, etc., or substantially so. Alternatively, the shape of housing 4 may be more complex such as a substantially irregular shape or the like.

The size of housing 4 may also vary depending on a variety of factors such as the type and size and shape of the testers to be used therewith, and the number of testers held or accommodated in housing 4, and the like. Usually, housing 4 is sized to be easily and comfortably held in a user's hand and easily transportable.

Housing 4 may be manufactured from a variety of materials, where such materials will not substantially interfere with the analyte concentration determination, e.g., will not substantially interfere with the reagents of the tester(s) held therein. Representative materials that may be used in the manufacture of the subject housing include, but are not limited to, polymeric materials such as polytetrafluoroethylene, polypropylene, polyethylene, polystyrene, polycarbonate and blends thereof, metals such as stainless steel, aluminum and alloys thereof, Teflon™, siliceous material, e.g., glass materials, and the like.

Figure 3:
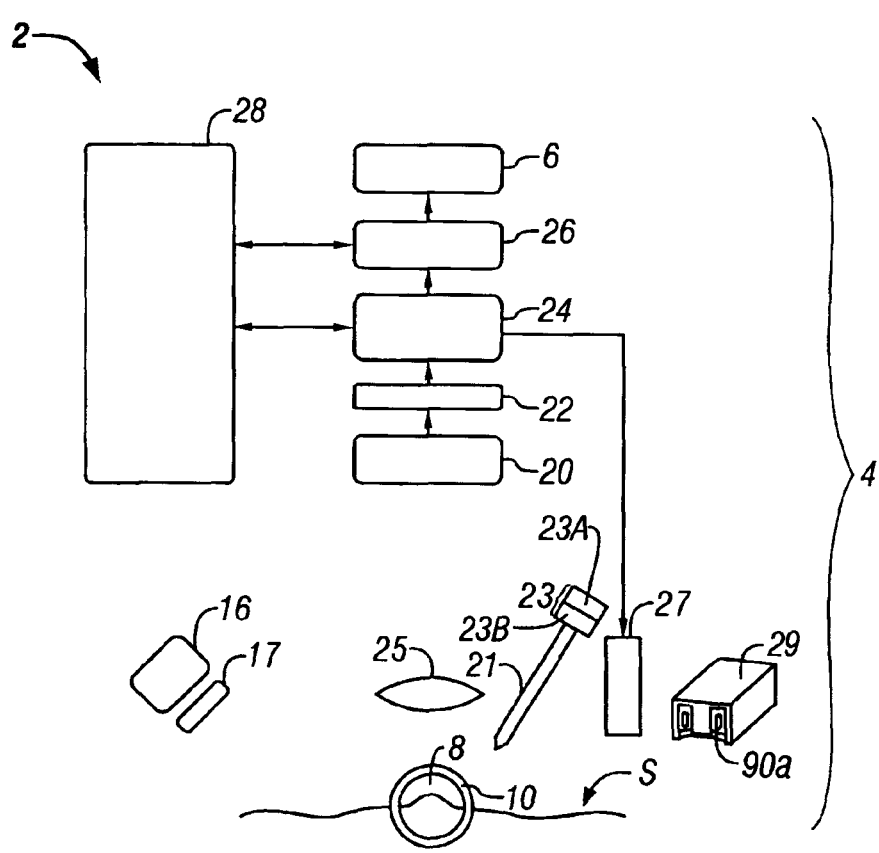
FIG. 3 is a schematic illustration of a subject device.

FIG. 3 shows a schematic illustration of device 2, and more specifically the internal components of housing 4. As shown, housing 4 is positioned on an area of skin S such that the area to be lanced is encompassed by aperture 8. Surrounding aperture 8, as mentioned above, is optional physiological sample promoting element 10 that is configured to increase the amount of the physiological sample at the area of skin to be incised. Sample promoting element 10 is usually configured as a ring or a partial ring that is capable of surrounding or substantially surrounding the area of skin to be incised to provide pressure to the surrounding area, thereby providing a bulged area to be incised, as shown. In such a manner, physiological fluid is displaced from the pressured area to areas adjacent the pressured areas, e.g., an area inside sample promoting ring 10, i.e., the area to be incised, and the area outside sample promoting ring 10, thereby engorging the area to be incised with physiological fluid. Pressure may be applied by the user, for example the user may push down on the device when contacted with skin or may be actuated automatically.

Housing 2 also includes lancing element 23 configured to hold a disposable lancet 21 for making an incision in an area of skin to provide physiological sample for testing, where disposable lancets are known in the art and will not be described further herein. As such, disposable lance 21 is capable of being actuated, either manually for example by depressing a button on housing 4 or automatically for example once the meter is positioned substantially close to an area of skin. As such, lancet 21 is moved from a first, resting position away from the skin to a second displaced position through aperture 8 and in contact with the skin, where it is caused to penetrate the skin to provide an incision therein to provide physiological sample from the incised site for testing.

Accordingly, lancing element 23 includes lancet holder 23a that retains disposable lancet 21 in a fixed position for lancing and lancet displacement mechanism 23b for displacing disposable lancet 21 towards the skin. Lancet holder 23a retains disposable lancet 21 using any suitable means such as friction, snap fit and the like, such that disposable lancet 21 is easily removable or ejectable for replacement with a new lancet, yet held firmly enough to avoid unintentional movement or ejection from lancet holder 23a. Lancet displacement mechanism 23b may use any convenient mechanism for displacing a lancet towards the skin, where such mechanisms are well known in the art. Lancet displacement mechanism 23b may be actuated automatically or manually, for example by some simple user action. For example, the motions could occur when user pushes a button on the meter or simply presses the meter against the test site. As for the workings of a meter able to produce the desired action, the design and production of certain actuators is well within the level of skill in the art. In certain embodiments, lancet displacement mechanism 23b is a spring mechanism such as a compression spring mechanism or the like (see for example U.S. Pat. No. 6,099,484, the disclosure of which is herein incorporated by reference). However, other suitable lancet displacement mechanisms may be employed and are well known in the art.

As shown, lancing element 23 with disposable lancet 21 is operatively positioned adjacent aperture 8 such that disposable lancet 21 is positioned in a first position away from the skin S, whereby upon actuation disposable lancet 21 is displaced to a second position through aperture 8 to make contact with and incise the skin. In this particular embodiment, lancing element 23 and thus disposable lancet 21 are positioned at an angle relative to aperture 8, however it will be apparent that lancing element 23 and disposable lancet 21 may be positioned in any appropriate orientation relative to aperture 8.

Housing 4 includes at least one light source 16 and typically also includes condensing lens 17 capable of focusing light from light source 16 to the area of aperture 8. Light source 16 projects light onto the area of the skin that has been incised by disposable lancet 12, that is it projects light onto the area of skin encompassed by aperture 8. Light source 16 also projects light onto a tester, e.g., the matrix of a tester, having sample applied thereto and which has reagents for reacting with certain analytes in the sample, as described above. The same or different light source may project light onto the skin as is used to project light onto a tester, where typically the same light source is used.

Accordingly, light source 16 typically includes a light emitting diode (LED) or any other convenient light source such as a laser diode, a filtered lamp, a phototransistor, and the like. Usually, the light source 16 contains two or more LED sources, e.g., three LED sources, or a single diode capable of emitting two or more distinct wavelengths of light. The light source 16 is usually capable of emitting light at wavelengths ranging from about 400 nm to about 1000 nm, usually from about 500 nm to about 940 nm.

For example, for illuminating an area of skin that has been incised for determining whether a sufficient amount of sample is present, light source 16 typically projects light at a wavelength of about 400 nm to about 1000 nm, more usually at about 480 nm to about 600 nm, where the hemoglobin with the blood sample absorbs light. For example, for illuminating a tester for analyte concentration determination where two distinct wavelengths are employed, the light source 16 is capable of emitting light at about 635 nm and about 700 nm and in many embodiments the light source is capable of emitting light at about 660 nm and 940 nm, and in certain embodiments the light source is capable of emitting light at about 525 nm, 630 nm and 940 nm. It will be apparent that the wavelengths described herein are for exemplary purposes only and are in no way intended to limit the scope of the invention as many other combinations of wavelengths are possible as well. Commercially available light sources that produce wavelengths of light described above are known in the art and include, but is not limited to, an LYS A676 light source capable of emitting light of 635 nm and 700 nm available from ASRAM Opto Semiconductor, Inc.

Housing 4 also includes at least one detector 20 for detecting light reflected from, i.e., intercepting reflected light, e.g., diffusely reflected light, the area of incised skin, for determining whether a sufficient amount of sample is present at the surface of the skin and for detecting light reflected, i.e., intercepting reflected light from, e.g., diffusely reflected light, a tester such as the matrix of a tester, for determining analyte concentration in a sample applied to the tester. The same or different detector may detect light from the above-described areas. Housing 4 may also include optional imaging optics 25 or an aperture (not shown) for imaging reflected light onto at least one detector 20.

The subject meters also include means for determining whether a sufficient amount or volume of sample is present at the surface of the skin that has had an incision made therein, where such determination is based upon the amount of reflected light detected from each area. This means is generally a digital integrated circuit 24, where such a digital integrated circuit 24 is under the control of a software program and thus is suitably programmed to execute all of the steps or functions required of it to determine whether reflected light indicates a sufficient amount of sample, or any hardware or software combination that will perform such required functions. That is, sample amount determination means 24 is capable of executing or following an algorithm stored in the meter to determine, based on reflected light detected from an area of skin and more specifically an area of skin having physiological sample thereon, whether a sufficient amount of sample is present to perform an accurate analyte concentration determination test. Sample amount determination means 24 usually reads the output of a signal conversion element such as analog/digital converter 22 which converts an analog signal from at least one detector 20 to a digital signal. Accordingly, sample amount determination means 24 is capable of carrying out all the steps necessary to determine whether reflected light detected from an area of skin indicates a sufficient amount of sample present in that area.

In addition to the above means for determining whether a sufficient amount of sample is present for perform an accurate analyte concentration determination analysis, the subject meters also include means for determining the concentration of an analyte in the sample 26, where such sample is contacted with a tester for analyte concentration determination. That is, if a sufficient amount of sample is determined to be present on the surface of the skin, the sample is contacted with a tester for analyte concentration determination, as will be described in greater detail below. This means is generally a digital integrated circuit 26, where such a digital integrated circuit 26 is under the control of a software program and thus is suitably programmed to execute all of the steps or functions required of it, or any hardware or software combination that will perform such required functions. That is, analyte concentration determination means 26 is capable of executing or following an algorithm stored in the meter to determine analyte concentration in a physiological; sample. (Analyte concentration determination means 26 is shown in FIG. 3 as a separate component from sample evaluation means 24, but in certain embodiments means for determining whether a sufficient amount of sample is present at the surface of the skin and means for determining the concentration of an analyte may be the same integrated circuit.) Accordingly, digital integrated circuit 26 is capable of carrying out all the steps necessary to determine analyte concentration in a physiological sample.

The subject meters also include program and data memory 28, which may be a digital integrated circuit, that stores data and the operating program of one or more of the digital integrated circuits of the meter. The subject meters also include reporting device 6, as described above, for communicating results of sample size sufficiency, analyte concentration, error messages, etc., to the user.

As mentioned above, if a sufficient amount of sample is determined to be present on the surface of an area of skin, the sample is contacted with a tester so that the concentration of an analyte in the sample may be determined. Accordingly, a tester, such as the type of tester described above or any appropriate tester such as the type of tester described below, is placed in contact with the sufficient amount of sample. A tester may be manually placed in contact with the sample or automatically moved into contact with sample. Accordingly, the subject meters usually include means for retaining at least one tester within housing 4, e.g., in an area or recess.

FIG. 3 shows an exemplary embodiment of tester cartridge or casing 29 having a plurality of testers 90 held therein, where tester 90a is positioned to be grasped so that it may be moved into an appropriate position.

Figure 4:
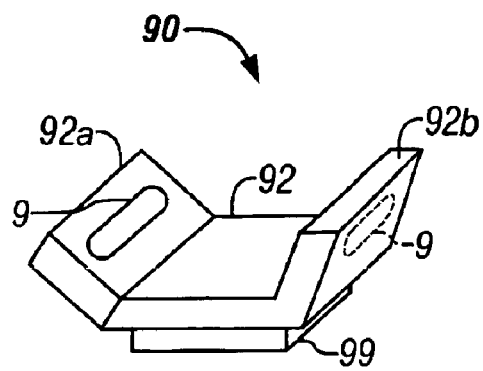
FIG. 4 shows an exemplary embodiment of a tester suitable for use with the subject invention.
Figure 5:
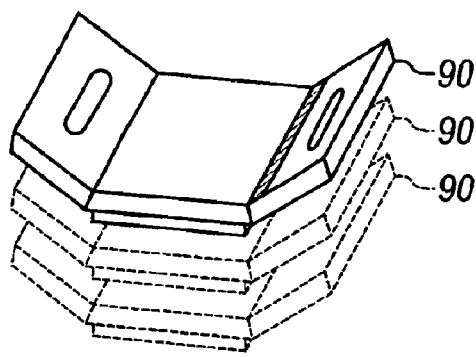
FIG. 5 shows a plurality of testers of FIG. 4 stacked together.
Figure 6:
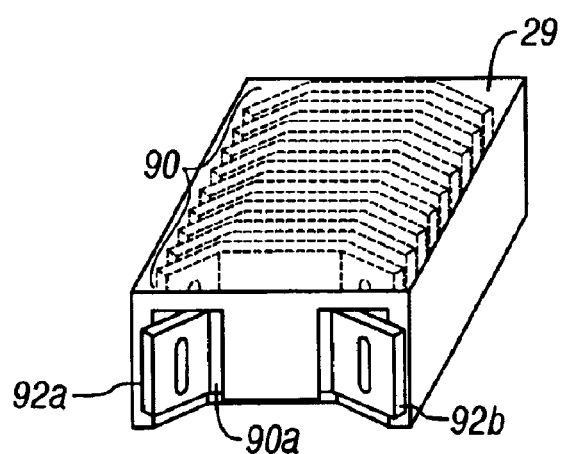
FIG. 6 shows the testers of FIG. 5 retained in a cartridge or casing.

In the particular embodiment shown in FIG. 3, the testers are configured to be easily grasped from cartridge 29. FIG. 4 shows an enlarged view of an exemplary embodiment of tester 90 suitable for use with the subject invention. As shown, tester 90 includes matrix 99 having members of a signal producing system (not shown as a structural component), where matrix 99 is attached to support 92. Support 92 has upwardly biased ends 92a and 92b, where in many embodiment ends 92a and 92b have grasping holes 9 therein or other convenient means to enable easy grasping. In many embodiments, support 92 includes a window or transparent area or the like (not shown) positioned over matrix 99 to enable light to illuminate matrix 99 and to enable light to be detected from matrix 99, through such a window or transparent area. In such a manner, tester 90 may be placed over a physiological sample and the matrix may be "read" at the opposite side of the matrix through the window or transparent area. Such testers also can be advantageously stacked for containment in a cartridge or casing, as shown in FIG. 5, and shown stacked in cartridge 29 in FIG. 6. As shown in FIG. 6, a plurality of testers 90 are retained within cartridge 29 and tester 90a is positioned to be accessible so that it may be grasped and moved to contact a sample. Such a tester configuration and cartridge are exemplary and in no way intended to limit the scope of the invention as other tester configurations and cartridges or containers housing such testers may be used with the present invention, as will be apparent to one of skill in the art.

As mentioned above, a tester is moved into contact with a sample determined to be present in a sufficient amount. As such, the subject meters may also include a tester movement element 27. A tester may be moved in any convenient manner, where the following embodiments are provided by way of example and are in no way intended to limit the scope of the invention. In all such embodiments, a tester is moved in contact with sample (i.e., sample is not moved to contact the tester), thus sample is not lost in the transfer process, as is the case with many prior art devices. When contacted with the sample, the absorbent matrix of the tester absorbs essentially all of the sample from the site. In such a manner, a smaller amount of sample present at the surface of skin is required for an accurate analyte concentration measurement than in many prior art devices.

An exemplary embodiment of a tester movement element suitable for use in the present invention is shown in FIGS. 7A–7F. Movement element 47 is associated with a wall W of housing 4 such that cam member 42 is slideably engaged with groove 40 of wall W. Cam member 42 is associated with one side of slideable movement member 43 by pin 45, where tester grasping arm 46 is associated with the other side of slideable movement member 43 by pin 48. As shown, slideable movement member 43 slideably moves along bar 41, in many embodiments which may be a groove or the like. In use, tester movement element 43 is actuated either manually or automatically, for example when a sufficient amount of sample is detected. Typically, tester movement element 43 is moved automatically by way of a motor or the like, but may also be moved manually such as by the action of a user slideably moving a button or knob on an exterior surface of housing 4 which is operatively associated with tester movement element 43. The steps of movement of such a tester are shown in FIGS. 7A–7F for moving tester 90a from cartridge 29, for example, to an area of skin S having physiological sample PS thereon. In the following figures, grasping arm 46 is not shown physically associated with tester 90a for the sake of showing an unobstructed view of the movement of tester 90a. It will be apparent that grasping arm 46 is associated with tester 90a, for example by holes 9 in tester 90a in order to move tester 90a to a site having physiological sample.

Figure 7A:
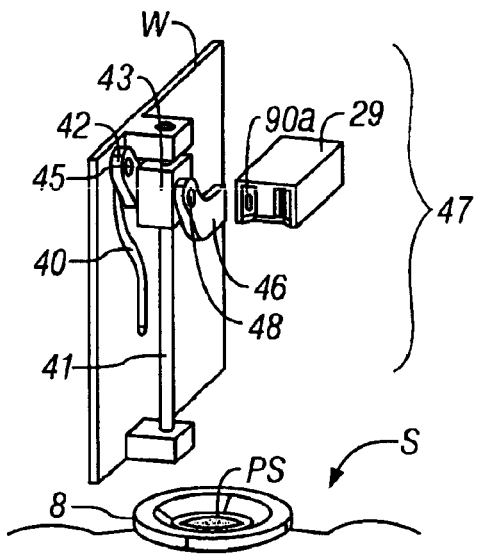
FIGS. 7A–7F shows the steps of an exemplary embodiment of a tester movement element moving a tester in contact with physiological sample present on the surface of skin.
Figure 7B:
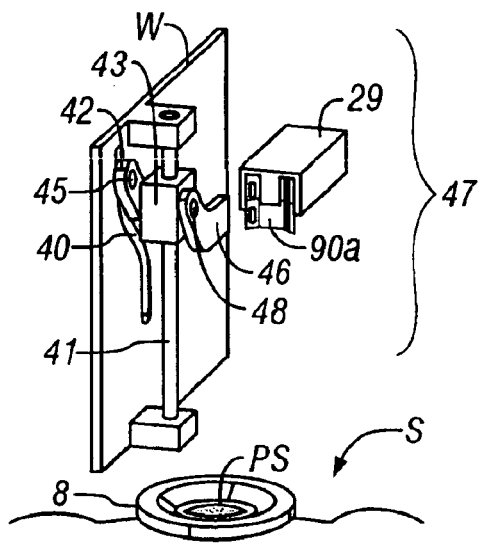
Figure 7C:
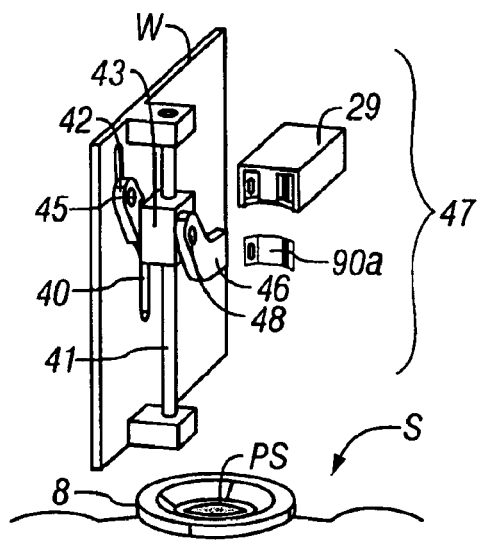
Figure 7D:
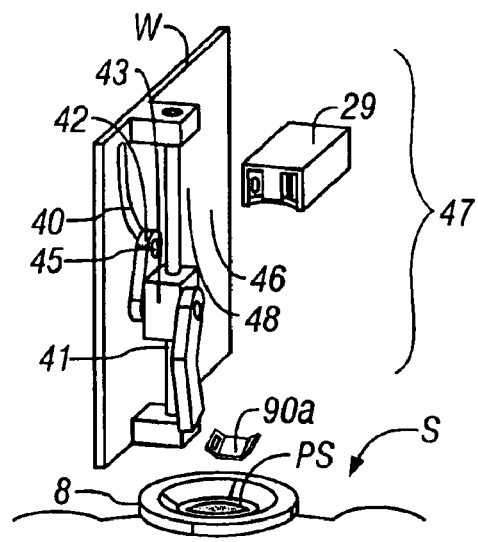
Figure 7E:
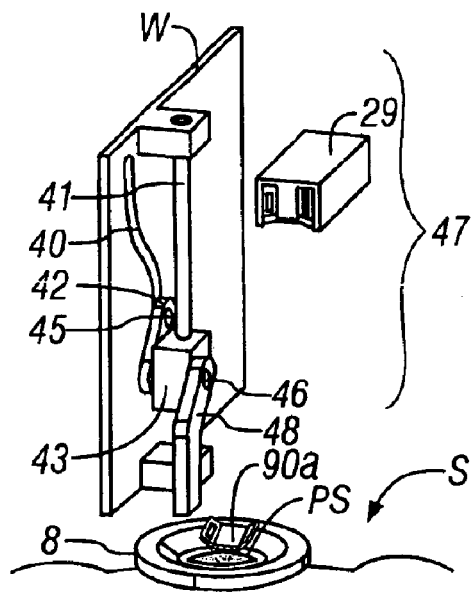
Figure 7F:
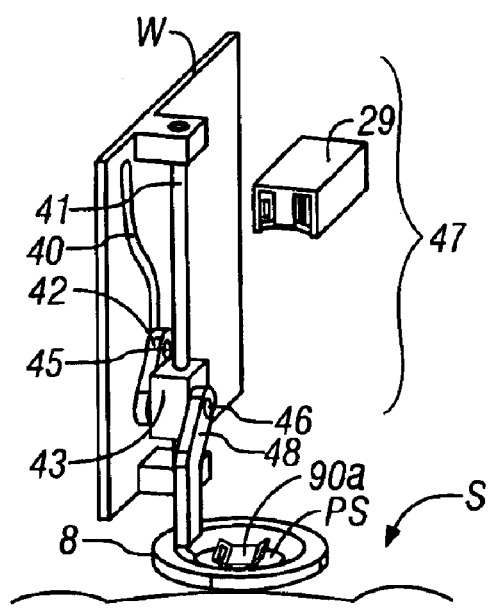

As shown in FIG. 7A, cam member 42 is positioned in a first position at the top of groove 40 and grasping arm 46 is operatively engaged with tester 90a which is in cartridge 29, but which is accessible to grasping arm 46. Cam member 42 slideably moves along groove 40 as slideable movement member 43 moves along bar 41. As slideable movement member 43 moves along bar 41 and cam member 42 slideably moves along groove 40, grasping arm 46 is caused to move tester 90a in a direction towards physiological sample PS, as shown in FIGS. 7A through 7F, where ultimately tester 90a is placed in contact with physiological sample PS when slideable movement member is in a second position at substantially the opposite end of bar 41 from the first position such that matrix 11 is positioned over physiological sample PS to absorb substantially all of the physiological sample. Grasping arm 46 is configured to hold tester 90a in contact with physiological sample PS and not obstruct the view of detector 20 or the path of the at least one light source 16 so that analyte concentration may be determined while the tester remains in the position, as shown in FIG. 7F.

Methods

Also provided by the subject invention are methods for determining the concentration of an analyte in a physiological sample applied to a tester. More specifically, methods are provided that enable the determination of whether a sufficient amount of physiological sample is present at the surface of an incised area of skin to perform an analyte concentration determination assay and, if such a sufficient amount of sample is present, a tester is contacted with the sample and the concentration of an analyte in the sample is determined.

As such, the first step is to lance an area of skin to provide physiological sample at the surface of the skin for testing. Any appropriate area of skin may be lanced, where typically a finger, forearm, toe, or the like are used. Accordingly, a subject device, as described above, having a disposable lancet 21 therein may be used to lance the skin by actuating lancing element 23, thereby displacing lancet 21 towards the skin such that lancet 21 protrudes through aperture 8 of housing 4 to provide an opening or incision in the skin.

In many embodiments, sample is caused to be present at the incised site by promoting the expression thereof. For example, force may be applied to the area of skin surrounding the area of interest from which physiological fluid is desired, either before or after lancing. As such, the area of interest becomes engorged with physiological fluid. In such a manner, a greater amount of sample may be provided from the incision than would be provided without the application of force to the perimeter of the area of interest. Accordingly, sample promoting element 10, as mentioned above, may be used to promote sample at the site.

Once physiological fluid is present at the surface of the skin, the sample is illuminated with light. For example, the sample may be illuminated with light at about 400 nm to about 1000 nm, usually about 480 nm to about 600 nm and more usually about 525 nm; however other wavelengths are possible as well as will be apparent to one of skill in the art. An important feature of the subject methods is that the size of the sample is determined to be sufficient or insufficient before the sample is contacted with a tester, based on the amount of reflected light from the sample. In this manner, a tester is not wasted due to insufficiency of sample applied thereto.

Accordingly, light is reflected from the sample at the surface of the skin, where such light is detected and related to the amount of physiological sample present. For example, skin reflects light at 525 nm, while hemoglobin present in a blood sample absorbs light at 525 nm. Accordingly, if a sufficient amount of sample is present, a significant amount of light will be absorbed by the hemoglobin and minimal or very little light will be reflected. Therefore, if the reflectance at 525 nm is sufficiently low or below a predetermined value or the like or is sufficiently reduced from an initial measurement reflectance value, for example taken at a time prior when sample is present, i.e., a measurement of light reflected from skin without blood present, it is determined that a sufficient amount of sample is present.

If present, imaging optics or an aperture may be used to image the reflected light onto a detector, as described above. The amount of sample determined to be sufficient will vary depending on a variety of factors such as the analyte of interest, the tester, etc. Typically, an amount of sample at the surface of the skin ranging from about 0.5 $\mu$l to about 10 $\mu$l is determined to be sufficient for obtaining accurate analyte measurements.

Accordingly, if it is determined that an insufficient amount of sample is present at the surface of the skin, analyte concentration is not performed with the present amount of sample. In such a case, a user may attempt to provide additional sample at the site, e.g., by milking the present incision or otherwise stimulating the site. If it is determined that a sufficient amount of sample is present at the surface of the skin, either initially or if additional sample has been provided after an initial determination of insufficiency as mentioned above, an analyte tester is contacted with the sufficient amount of sample at the surface of the skin. Accordingly, an important feature of the subject invention is that the sample is not moved to the site of the tester, rather the tester is moved to the site of the sample. In this way, sample is not lost in the transfer process, for example to the sides of a capillary tube or needle or the like. As such, a minimal amount of sample is required at the surface of the skin for accurate analyte concentration determination, where the amount may be as little as about 0.5 µl, as described above. Specifically, a tester is brought into contact with the sample such that sample is absorbed directly onto the tester, without the aid of a transfer tube or the like.

In using a subject device, the tester is usually moved into an operative position relative to the sample using tester movement element 27. For example, as described above, at least one tester, usually a plurality of testers, is retained inside housing 4, typically in a cartridge 29 or the like. Tester movement element 27 engages a topmost or first tester 90a positioned in cartridge 29 such that tester 90a is accessible to tester movement element 27 and any remaining testers 90 are positioned or stacked inside cartridge 29 for use at a later time, where once tester 90a is removed from cartridge 29, the next tester positioned behind tester 90a will move into position to be grasped and moved. As such, test strip movement element 27 grasps tester 90a and moves it into contact with the physiological sample, (see FIGS. 7A–7F).

Once a tester is contacted with the sample, the sample is allowed to react with the members of the signal producing system to produce a detectable product that is present in an amount proportional to the initial amount of analyte present in the sample. The amount of detectable product, i.e., signal produced by the signal producing system, is then determined and related to the amount of analyte in the initial sample. In using a subject device, means for determining the concentration of an analyte in the sample 26 determines analyte concentration, as described above, where the results of the analyte concentration determination are communicated to a user by reporting element 6.

Kits

Finally, kits for practicing the subject methods are provided. The subject kits include a device according to the subject invention, i.e., a subject optical meter. The subject kits may also include one or more testers, usually a plurality of testers retained in a cartridge or the like, such as the type of tester described above. The subject kits may further include one or more disposable lancets. In addition, the subject kits may include a control solution or standard, e.g., a control solution that has a known analyte concentration such as a known glucose concentration. The kits may further include instructions for using the apparatus for determining the presence and/or concentration of an analyte in a physiological sample applied to a tester. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides a simple, quick and convenient way to determine whether a sufficient amount of sample is present for analyte concentration determination and to determine analyte concentration in a sample determined to be present in a sufficient amount. The above described invention provides a number of advantages, including, but not limited to, integration of several testing components in a single, hand-held device, ease of use, determination of whether a sufficient amount of sample is present before contacting the sample with a tester and accurate analyte concentration determination using minimal sample amounts. As such, the subject invention represents a significant contribution to the art.

The subject invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A method for determining the concentration of an analyte in a physiological sample, said method comprising:
    (a) lancing an area of skin to provide a physiological sample at the surface of said area of skin;
    (b) illuminating said physiological sample present at said surface of skin;
    (c) detecting light reflected from said physiological sample present at said surface of skin; and
    (d) determining whether said physiological sample is present at said surface of said skin in an amount sufficient for analyte concentration determination based upon said detected reflected light.

2. The method according to claim 1, further comprising determining the concentration of an analyte in said physiological sample determined to be present in a sufficient amount, wherein analyte concentration is not determined if an insufficient amount of sample is not present.

3. The method according to claim 2, wherein said analyte concentration determination comprises moving a tester in contact with said physiological sample determined to be present in a sufficient amount, wherein a tester is not moved into contact with said physiological sample determined to be present in an insufficient amount.

4. The method according to claim 1, further comprising increasing the amount of physiological fluid expressed from said incised area of skin by applying a force to the perimeter of incised said area, thereby increasing the amount of said physiological fluid at said incised site.

* * * * *